United States Patent [19]

Mezrich et al.

[11] 4,242,913
[45] Jan. 6, 1981

[54] ACOUSTIC VARIABLE FOCAL LENGTH LENS ASSEMBLY

[75] Inventors: Reuben S. Mezrich, Rocky Hill; Wilber C. Stewart, Hightstown, both of N.J.

[73] Assignee: RCA Corporation, New York, N.Y.

[21] Appl. No.: 109,511

[22] Filed: Jan. 4, 1980

Related U.S. Application Data

[63] Continuation of Ser. No. 963,806, Nov. 30, 1978, abandoned.

[30] Foreign Application Priority Data

Dec. 12, 1977 [GB] United Kingdom ............... 51687/77

[51] Int. Cl.$^3$ ............................................. G01N 29/00
[52] U.S. Cl. .................................................... 73/626
[58] Field of Search .............. 73/626, 625, 628, 642; 128/660; 367/103, 105

[56] References Cited

U.S. PATENT DOCUMENTS

| | | | |
|---|---|---|---|
| 3,936,791 | 2/1976 | Kossoff | 73/626 |
| 4,019,169 | 4/1977 | Takamizawa | 73/626 |
| 4,058,003 | 11/1977 | Macovski | 73/626 |
| 4,080,838 | 3/1978 | Kuroda et al. | 73/626 |
| 4,131,022 | 12/1978 | Mezrich | 73/625 |

*Primary Examiner*—Stephen A. Kreitman
*Attorney, Agent, or Firm*—Samuel Cohen; George J. Seligsohn

[57] ABSTRACT

A lens assembly exhibiting a certain fixed relative aperture is comprised of a physical acoustic lens having a given physical aperture and a fixed relatively short focal length serially spaced from an electronic acoustic lens having any selected one of a plurality of different relatively long focal lengths and simultaneously controlling the physical aperture of the electronic acoustic lens such that the relative aperture of the assembly as a whole remains fixed regardless of the selected one of the long focal lengths. Such a lens assembly is suitable for use in a pulse-echo ultrasonic-imaging system for imaging a deep structure.

8 Claims, 7 Drawing Figures

ACOUSTIC VARIABLE FOCAL LENGTH LENS ASSEMBLY

This is a continuation of application Ser. No. 963,806, filed Nov. 30, 1978, now abandoned.

This invention relates to an acoustic variable focal length lens assembly and, more particularly, to such a lens assembly which is suitable for use in an ultrasonic pulse-echo imaging system for imaging a deep structure.

Reference is made to currently allowed U.S. patent application Ser. No. 766,527, filed Feb. 7, 1977 by Mezrich now U.S. Pat. No. 4,131,022, and assigned to the same assignee as the present application. It discloses a pulse-echo ultrasonic-imaging display system incorporating an acoustic lens having a fixed focal length f and a physical aperture A. (The term "physical aperture", as used herein, means the maximum linear dimension of the cross section of the lens measured in the same units of distance as the focal length. The "relative aperture" of the lens, defined as A/f, is dimensionless.) The acoustic lens is used to focus a beam of ultrasonic wave energy having a predetermined wavelength $\lambda$. This beam is normally at least as wide as the physical aperture A, so that the entire cross section of the acoustic lens operates on the ultrasonic wave energy.

As disclosed in patent application Ser. No. 766,527, the imaging resolution is directly proportional to the value of the wavelength $\lambda$ of the ultrasonic wave energy and is inversely proportional to the value of the relative aperture A/f. Thus, the larger the relative aperture, the higher the imaging resolution (i.e., the smaller the size of the spot that can be resolved) that is obtainable with ultrasonic wave energy of a given wavelength. However, while the depth of field of an acoustic lens is also proportional to the wavelength of the ultrasonic wave energy, it is inversely proportional to the square of the relative aperture. However, due to the relatively long wavelength of ultrasonic wave energy propagated in a liquid (e.g. in the order of 1 mm), an acoustic lens having a relatively large relative aperture (e.g. $\frac{1}{3}$ to $\frac{1}{2}$) exhibits good resolution with an appreciable depth of focus. Furthermore, since the resolution decreases only linearly with a decrease in relative aperture, but the depth of field increases in accordance with the square of the decrease in the relative aperture, a relatively large increase in depth of field can be achieved at a relatively low cost in loss of resolution.

Reference is also made to currently-allowed U.S. patent application Ser. No. 844,140, filed Oct. 20, 1977 by Mezrich, now U.S. Pat. No. 4,138,895 and assigned to the same assignee as the present application. It discloses an electro-acoustic transducer, comprising a slab of piezoelectric material having a common electrode on one face thereof and a center electrode surrounded by an annular electrode on the other face thereof. The physical aperture of the center and annular electrodes, taken together, is large enough to provide a beam of ultrasonic wave energy having a width sufficient to substantially insonify the entire physical aperture of a relatively-large relative aperture acoustic lens. However, the center electrode, alone, provides a beam of ultrasonic wave energy having a width only sufficient to insonify a relatively small central portion of the physical aperture of the acoustic lens. Switch means are provided for selectively utilizing the center electrode alone, or, alternatively, utilizing both the center and annular electrodes together. The relatively large effective relative aperture (and, hence, a relatively small depth of field) provided by the center and annular electrodes together is useful in providing a relatively high resolution C-scan display of an ultrasonic image of a small depth of insonified structure. The relatively small effective relative aperture (and hence the relatively large depth of field) obtained by employing the center electrode alone is useful in providing a somewhat lower resolution B-scan display of an ultrasonic image of a larger depth of insonified structure.

The present invention is directed to an acoustic variable focal length lens assembly comprising first and second spaced acoustic lenses for focusing acoustic wave energy of a predetermined wavelength. The first acoustic lens has a single relatively short predetermined focal length, while the second acoustic lens is electronically controlled to have any selected one of a predetermined plural number of different preselected discrete focal lengths. Each of these discrete focal lengths is substantially larger than the predetermined focal length of the first acoustic lens. Such an acoustic, variable focal length lens assembly is particularly suitable for use in an ultrasonic pulse-echo imaging system for imaging deep structure insonified with a pulse of ultrasonic wave energy of a predetermined wavelength. In this case, time-control means responsive to the time of transmission of a pulse of ultrasonic wave energy, is coupled to the second lens for sequentially selecting each of the different discrete focal lengths during the time in which ultrasonic echos are received from successive portions of the insonified deep structure. This provides an effective resultant depth of field for the lens assembly which includes the entire depth of the deep structure to be imaged.

Figure 1:
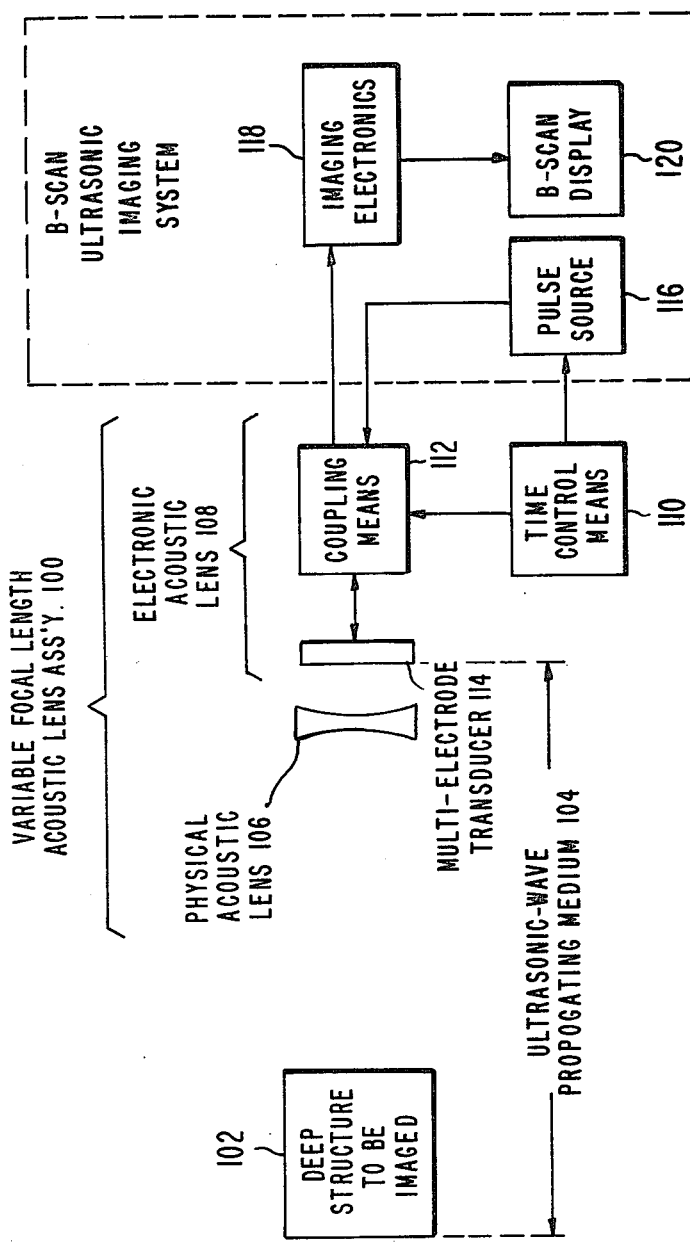
FIG. 1 is a block diagram of a pulse-echo ultrasonic-imaging display system incorporating a variable focal length acoustic lens assembly embodying the present invention.

For illustrative purposes, FIG. 1 shows a B-scan ultrasonic imaging system. However, it should be understood that the present invention may be incorporated in an ultrasonic imaging system employing both a B-scan and a C-scan. Alternatively, the invention may be incorporated in an ultrasonic imaging system incorporating only C-scan which employs the variable focal length acoustic lens assembly of the present invention to provide a resultant depth of field sufficient to image all points within a deep structure with good focus.

In FIG. 1, variable focal length acoustic lens assembly 100, which forms the principal subject matter of the present invention, is utilized to insonify deep structure to be imaged 102 with a focused scanning beam of pulsed ultrasonic wave energy of a predetermined wavelength traveling in ultrasonic wave propagating medium 104. As shown in FIG. 1, variable focal length acoustic lens assembly 100 comprises serially spaced physical acoustic lens 106 and electronic acoustic lens 108. Electronic acoustic lens 108 comprises time-control means 110, coupling means 112 and multi-electrode tranducer 114.

Preferably, physical acoustic lens 106, which is comprised of a solid material (such as polystyrene) having an acoustic index of refraction less than that of a surrounding ultrasonic-wave propagating medium 104 (such as water), is fixed in position. In this case, scanning of structure to be imaged 102 with a beam of ultrasonic wave energy is achieved by either moving only multi-electrode transducer 114 or employing auxiliary scanning means, such as Risley prisms (not shown). However, the present invention also contemplates moving both physical acoustic lens 106 and electronic acoustic lens 108 to achieve scanning of structure to be imaged 102 with a beam of ultrasonic wave energy.

Time-control means 110 includes a clock for intermittently applying a keying pulse to pulse source 116 of a B-scan ultrasonic imaging system. Pulse source 116 includes an R.F. oscillator for applying a pulse of ultrasonic frequency (e.g. 1.5 MHz) through coupling means 112 to multi-electrode transducer 114 in response to each keying pulse from time-control means 110.

The respective structure of multi-electrode transducer 114 and of coupling means 112 (embodiments of which are shown in FIGS. 2a, 2b and 3, 3a and 3b) is discussed in detail below. At this point, it is sufficient to say that, in response to the application thereto of an ultrasonic-frequency pulse from pulse source 116, multi-electrode transducer 114 launches a beam of pulsed ultrasonic wave energy having a selected one of a predetermined plural number of preselected discrete focal lengths, each of the discrete focal lengths being substantially larger than the single relatively-short predetermined focal length of physical acoustic lens 106.

Deep structure 102, in response to the insonification thereof, emits an echo, some of which returns through physical acoustic lens 106 to multielectrode transducer 114, giving rise, in turn, to detected electrical signals. Coupling means 112, under the control of time-control means 110, couples only those signals which occur during a certain time interval following the insonification of deep structure 102 through imaging electronics 118 to B-scan display 120 of the imaging system.

It is essential that the entire depth of structure 102 be within the total depth of field of lens assembly 100 in order to image all of deep structure 102 on B-scan display 120. However, structure 102 has a depth which is greater than the depth of field of any selected single focal length of lens assembly 100. In order to achieve the required total depth of field of lens assembly 100, coupling means 112 sequentially selects, under the control of time-control means 110, each of different discrete focal lengths of electronic acoustic lens 108, during each of successive portions of the aforesaid certain time interval, to provide an effective resultant depth of field for variable focal length acoustic lens assembly 100 which includes the entire depth of deep structure 102. In order to more fully understand the manner in which this is accomplished, reference is made to FIGS. 2a, 2b, 3, 3a and 3b.

Figure 2A:
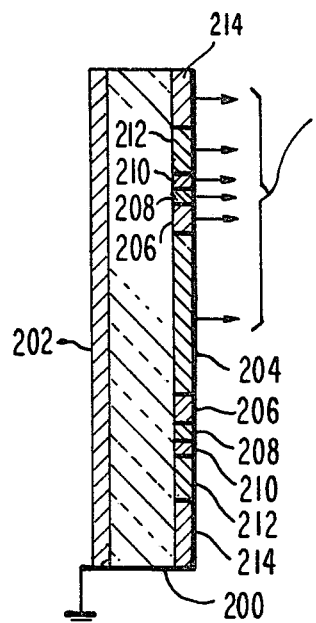
FIGS. 2a and 2b are a cross-section and plan view, respectively, of an embodiment of the multi-electrode transducer portion of the electronic acoustic lens of FIG. 1.
Figure 2B:
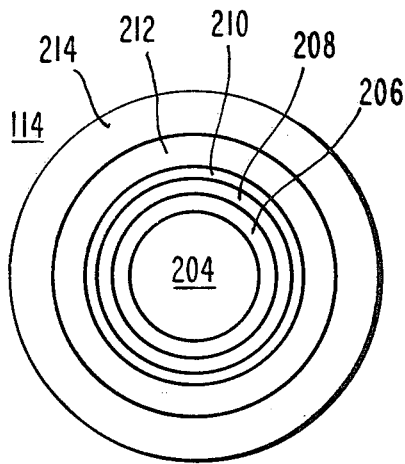

As shown in FIGS. 2a and 2b, multi-electrode transducer 114 comprises a slab of piezoelectric material 200 having its faces covered by a plurality of electrodes. Specifically, common electrode 202 substantially covers one of the two opposite faces of slab 200, while the other of the two opposte faces of slab 200 is substantially covered by a plurality of separate spatially distributed contiguous electrodes 204, 206, 208, 210, 212 and 214. As shown in FIGS. 2a and 2b, electrode 204 is a center electrode having a circular cross section of a preselected diamter and is surrounded, in turn, by contiguous annular electrodes 206, 208, 210, 212 and 214. Electrodes 204 . . . 214 substantially cover the entire cross section defined by the outer diamter of outermost electrode 214 (i.e., the inner diamater of each annular electrode is substantially equal to the outer diameter of the electrode that it immediately surrounds). As indicated in FIGS. 2a and 2b, the radial widths (the difference between the inner and outer radii of the respective annular electrodes 206 . . . 214) are different from each other and are different from the diameter of center electrode 204. The reason for these different radial widths is discussed below.

Figures 3A, 3B:
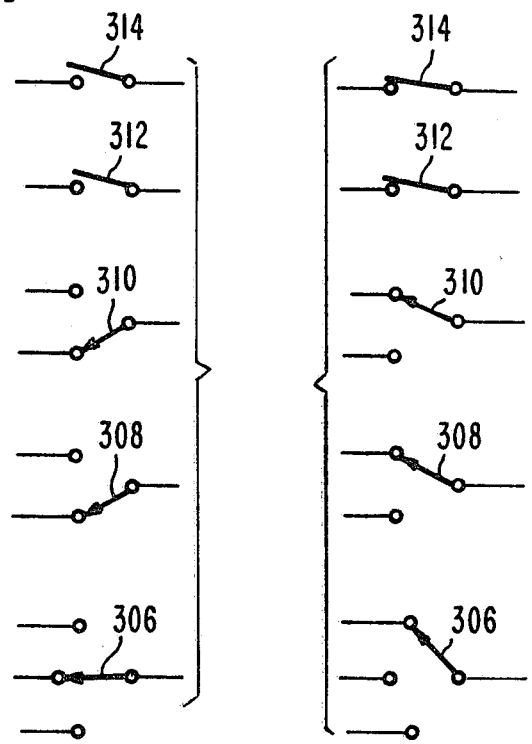
FIGS. 3a and 3b show a portion of FIG. 3 and are referred to in the explanation of its operaion.
Figure 3:
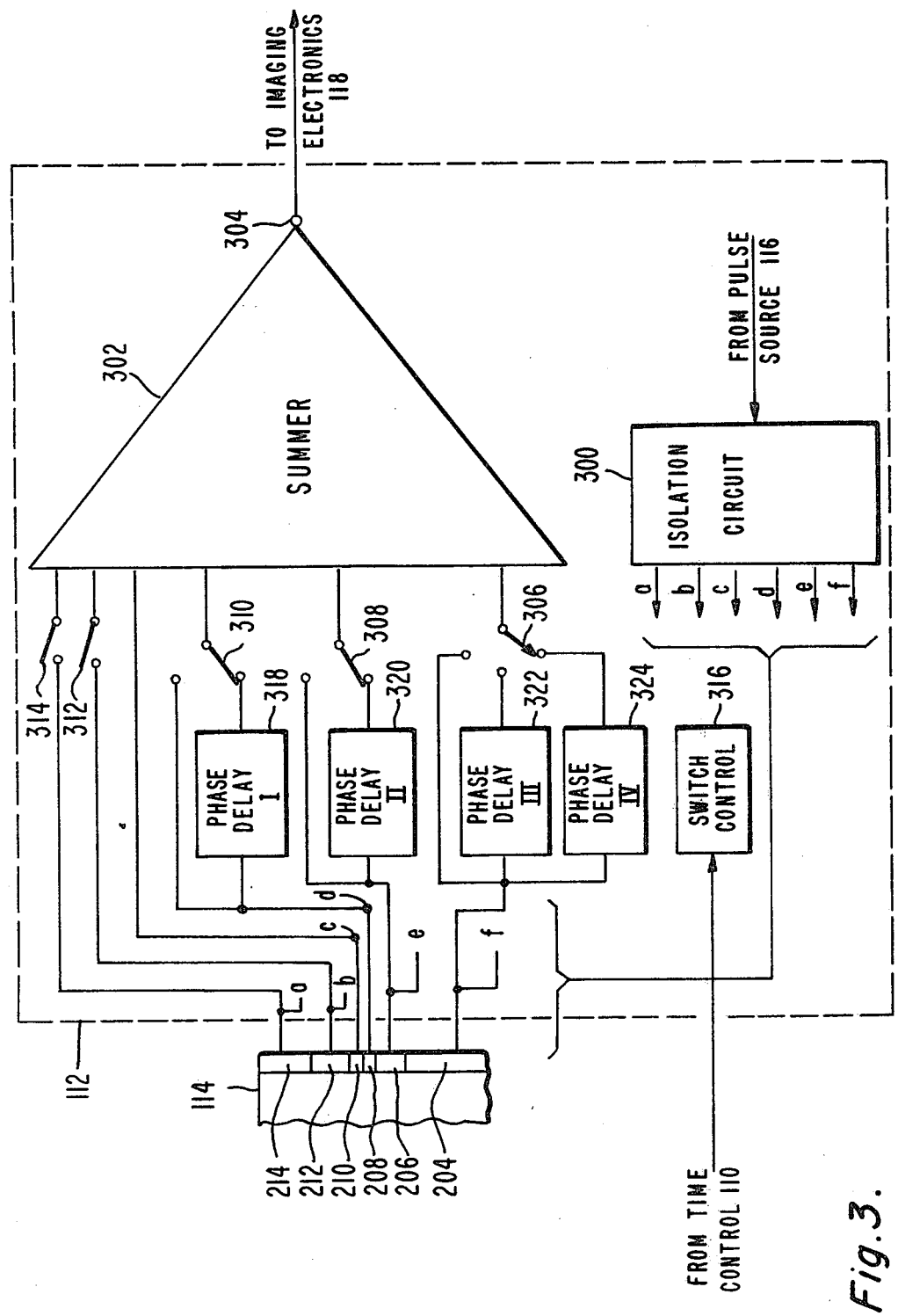
FIG. 3 is a block diagram of an embodiment of the coupling means portion of the electronic acoustic lens of FIG. 1.

As shown in FIG. 2a and FIG. 3, common electrode 202 is grounded and each of electrodes 204 . . . 214 is separately connected to coupling means 112. Coupling means 112, shown in FIG. 3, comprises isolation circuit 300, which operates as a transmit-receive switch. Circuit 300 permits ultrasonic frequency pulses from pulse source 116 to be forwarded to each of electrodes 204 . . . 214 of transducer 114, but prevents received signals on electrodes 204 . . . 214 from being returned to pulse source 116. By way of example, isolation circuit 300 may comprise a threshold switch (of a type disclosed in the aforesaid application Ser. No. 844,140) consisting of oppositely-poled semiconductor diodes. Such a threshold switch permits each ultrasonic frequency pulse from pulse source 116, which pulses have absolute values of amplitude greater than a semiconductor threshold voltage (e.g. 0.7 volts), to be coupled in parallel to all of electrodes 204 . . . 214. However, since the amplitude of received signals is always much below this threshold voltage, received signals are isolated from pulse source 116.

If, as has been assumed in the above example, each ultrasonic frequency pulse is applied in parallel to all of electrodes 204 . . . 214 of transducer 114, transducer 114 operates to launch a plane wavefront of ultrasonic wave energy in propagating medium 104; i.e., the focal length of the electronic lens 108, in this case, is infinity.

Coupling means 112 also includes switch means and phase delay circuits for coupling any of selected combinations of electrodes 204 . . . 214 through summer 302 to a common terminal 204 (at the output of summer 302) connected to imaging electronics 118. In order to clarify the description of the operation of the switch means, the switch means in FIG. 3 is functionally shown as comprising triple-throw switch 306, coupling electrode 204 to a first input of summer 302; double-throw switch 308, coupling electrode 206 to a second input of summer 302; double-throw switch 310, coupling electrode 208 to a third input of summer 302; single-throw switch 312, coupling electrode 312 to a fifth input of summer 302, and single-throw switch 312, coupling electrode 214 to a sixth input of summer 302. (As shown in FIG. 3, electrode 210 is connected directly to a fourth input of summer 302). Functionally, these switch means also include switch control 316 for selectively operating switches 306, 308, 310, 312 and 314 in accordance with time control signals applied thereto from time control 110. It should be understood that in actual practice the switch means normally would comprise a plurality of normally-closed electronic gates which are selectively opened in any of various predetermined combinations in accordance with applied time-control signals from time control 110. However, the operation of these electronics gates would be functionally equivalent in all respects to the operaation of switches 306, 308, 310, 312 and 314, described in detail below.

Coupling means 112 also includes a plurality of phase delay circuits. Specifically, when double-throw switch 310 is in its upper switch position, any signal appearing on electrode 208 is coupled to the third input of summer 302 without any phase delay. However, when double-throw switch 310 is in its lower switch position, any signal appearing on electrode 208 is coupled to the third input of summer 302 with a phase delay of one-quarter cycle of the ultrasonic frequency, which is provided by phase delay I circuit 318. In a similar manner, any signal on electrode 206 is coupled to the second input of summer 302 without a phase delay when double-throw switch 308 is in its upper switch position or, alternatively, with a phase delay of one-quarter cycle of the ultrasonic frequency, which is provided by phase delay II circuit 320, when double-throw switch 308 is in its lower switch position. Further, any signal on electrode 204 is coupled to the first input of summer 302 without phase delay, when triple-throw switch 306 is in its upper switch position, or with a phase delay of one-quarter cycle of the ultrasonic frequency, which is provided by a phase delay III circuit 322, when triple-throw switch 306 is in its middle switch position, or with a phase delay of one-half cycle of the ultrasonic frequency, which is provided by phase delay IV circuit 324, when triple-throw switch 306 is in its lower switch position.

The present invention makes use of certain known optical relationships, which will now be discussed. First, the resultant focal length f of a lens assembly consisting of a first lens having a focal length $f_1$ in serial spaced relationship with a second lens having a focal length $f_2$ is given by the following equation:

$$\frac{1}{f} = \frac{1}{f_1} + \frac{1}{f_2} \quad (1)$$

Second, a physical imaging lens operates by phase delaying an incident wavefront by an amount which varies continuously as an inverse function of the distance between every point of incidence of the wavefront and the lens axis. An electronic lens, of the type shown in FIGS. 2a, 2b, 3, 3a and 3b, utilizes a certain finite number of discrete electrodes associated with a discrete finite number of electrical phase delay circuits to simulate the operation of a physical lens. Such an electronic lens would require an infinite number of electrodes placed infinitely close together (which is impossible) in order to exactly duplicate a physical lens. However, as is known (in accordance with the Rayleigh condition), a lens in which the phase delay varies inversely as a discontinuous function of off-axis distance still operates to produce an image, without appreciable degradation, so long as the phase delay provided for every point of incidence of the wavefront does not depart from that provided by the continuously varying phase delay of a physical lens by more than one-quarter wavelength of the incident wave (i.e., one-quarter cycle of the ultrasonic frequency). An electronic lens of the type shown in FIGS. 1, 2a, 3, 3a and 3b is designed in accordance with this Rayleigh condition.

It can be shown that an electronic lens comprising a transducer having n electrically separate concentric electrodes on a face thereof exhibits a focal length $f_2$ and complies with the Rayleigh condition for an incident wavefront of ultrasonic energy having a wavelength $\lambda$, if the respective outer radii $r_1 \ldots r_n$ of the respective n electrodes conform with the following equations:

$$r_1 = [\frac{f_2 \lambda}{2}]^{\frac{1}{2}} \quad (2\text{-}1)$$

$$r_2 = [\frac{2 f_2 \lambda}{2}]^{\frac{1}{2}} \quad (2\text{-}2)$$

$$r_n = [\frac{n f_2 \lambda}{2}]^{\frac{1}{2}} \quad (2\text{-}n)$$

Since it is the purpose of the present ivention to selectively provide any one of a plurality of different focal lengths, a different set of radii $r_1 \ldots r_n$ electrodes are required for each different focal length. Further, it is required that the relative aperture of the lens have a substantially constant value (i.e., be substantially independent of the selected focal length). To meet these requirements, the electronic lens transducer must have a sufficient number of contiguous concentric electrodes on a face thereof; each electrode having an appropriate radial width, to permit each different set of radii for each different focal length to be achieved by selectively connecting at least some of the electrodes in one or more groups, with each group consisting of one or more electrodes connected in parallel. This results in the radial width of some of the electrodes being relatively small. The actual size of the radial widths of the electrodes depends on the respective sizes of the required different focal lengths.

In particular, equations 2-1 . . . 2-n show that the respective sizes of $r_1 \ldots r_n$ vary directly as a function of the size of the focal length $f_2$. Thus, when all of the plural number of focal lengths selectable by the electronic lens are large in size, the minimum size of the radial width of the concentric electrodes of the electronic lens required to derive these focal lengths becomes greater. It is for this reason that the present invention, in accordance with equation 1, combines a variable relatively-long focal length electronic acoustic lens with a fixed relatively-short focal length physical acoustic lens to achieve a variable relatively-short focal length acoustic lens assembly. Further, the value n, and hence the total number of required electrodes, is reduced, because the relative aperture of the variable relatively-long focal length electronic acoustic lens alone becomes small with respect to the desired relative aperture of the variable relatively-short focal length acoustic lens assembly.

For illustrative purposes in explaining the operation of the present invention, it is assumed that the ultrasonic wave energy has a wavelength $\lambda$ of 1 mm. It is also assumed that variable focal length acoustic lens assembly 100 is designed to have a selectable focal length of 150 mm, 200 mm, or 250 mm, with a substantially constant relative aperture of one-third. It is further assumed that physical acoustic lens 106 has a fixed focal length of 250 mm and a physical aperture which at least as large as the maximum physical aperture of electronic acoustic lens 108, so that the physical aperture exhibited by electronic acoustic lens 108 determines the physical aperture of variable focal length acoustic lens assembly 100.

With these assumptions, equation 1 may be employed to determine the different relatively long focal lengths required of electronic acoustic lens 108. Specifically, with a 250 mm focal length physical lens 106, the respective focal lengths of electronic lens 108 must be 375 mm, 1000 mm, or infinity in order to derive respective focal lengths of 150 mm, 200 mm, or 250 mm for lens assembly 100. Further, since the physical aperture of lens assembly 100 is determined by the physical aperture of electronic lens 108, electronic lens 108 must have respective physical apertures of 50 mm, 66.7 mm, or 83.3 mm for the respective focal lengths of 150 mm, 200 mm, or 250 mm of lens assembly 100, in order for lens assembly 100 to always have a relative aperture of substantially one-third.

The respective radial widths and outer radii of electrodes 204 . . . 214, which permits any one of the three assumed focal lengths of electronic lens 108 (together with its corresponding physical aperture) to be selected in accordance with the settings of switches 306 . . . 314, is listed below in Table 1.

TABLE 1

| Electrode | Radial Width | Outer Radius |
|---|---|---|
| 204 | 13.69 | 13.69 |
| 206 | 5.67 | 19.36 |
| 208 | 3.00 | 22.36 |
| 210 | 1.36 | 23.72 |
| 212 | 7.90 | 31.62 |
| 214 | 10.05 | 41.67 |

Specifically, switch control 316 places switches 306 . . . 314 into a selected one of three given combinations of switch settings, each different combination corresponding to a different one of the three assumed focal lengths (and corresponding physical aperture) of electronic lens 108. FIG. 3 shows a first given combination of settings of switches 306 . . . 314, which selects a focal length of 375 mm for electronic lens 108. In this first combination, single-throw switches 314 and 312 are open, so that signals at electrodes 214 and 212 are not coupled to summer 302. Double-throw switch 310 is in its upper switch position, so that signals at electrode 208 are coupled directly to summer 302. Double-throw switch 308 is in its lower switch position, so that signals at electrode 206 are coupled to summer 302 through phase delay II circuit 320 with a phase delay of one-quarter cycle of the ultrasonic frequency. Triple-throw switch 306 is in its lower switch position, so that signals at electrode 204 are coupled through phase delay IV circuit 324 to summer 302 with a phase delay of one-half cycle of the ultrasonic frequency.

Table 2 below, shows the assumed conditions for this first switch combination. The respective outer radii 13.69, 19.36 and 23.72 mm (shown in Table 2) correspond to the respective values, $r_1$, $r_2$ and $r_3$ of equations 2-1 . . . 2-n, when a focal length of 375 mm is substituted for $f_2$ and 1 mm is substituted for $\lambda$. Further, the actual physical aperture of electronic lens 108 in its first switch combination is 47.44 mm (i.e., double the outermost radius of 23.72 mm). This is substantially equal to the design criteria physical aperture of 50 mm.

TABLE 2

| | First Switch Combination | | |
|---|---|---|---|
| 1. | Lens Assembly 100 (Design Criteria) | Focal Length Physical Aperture Relative Aperture | 150 mm 50 mm ⅓ |
| 2. | Physical Lens 106 | Focal Length | 250 mm |

TABLE 2-continued

| | First Switch Combination | | |
|---|---|---|---|
| | | Physical Aperture | at least 83.3 mm |
| 3. | Electronic Lens 108 (Design Criteria) | Focal Length Physical Aperture | 375 mm 50 mm |
| 4. | Effective Electrodes | Radial Width | Outer Radius | Phase Delay |
| | 204 | 13.69 mm | 13.69 mm | ½ cycle |
| | 206 | 5.67 | 19.36 | ¼ |
| | 208 & 210 | 4.36 | 23.72 | 0 |

FIG. 3a shows a second given combination of settings of switches 306 . . . 314, which selects a focal length of 1000 mm for electronic lens 108. In the second combination, single-throw switch 314 is open, so that signals at electrode 214 are not coupled to summer 302. Single-throw switch 312 is closed, so that signals at electrode 212 are coupled directly to summer 302. Double-throw switch 310 is in its lower switch position, so that signals at electrode 208 are coupled to summer 302 through phase delay I circuit 318 with a phase delay of one-quarter cycle of the ultrasonic frequency. Double-throw switch 308 is in its lower switch position, so that signals at electrode 206 are coupled to summer 306 through phase delay II circuit 320 with a phase delay of one-quarter cycle of the ultrasonic frequency. Triple-throw switch 306 is in its middle switch position, so that signals at electrode 204 are coupled through phase delay II circuit 322 to summer 302 with a phase delay of one-quarter cycle of the ultrasonic frequency.

Table 3, below, shows the assumed conditions for this second switch combination. The respective outer radii 22.36 and 31.62 mm (shown in Table 3) correspond to the respective values $r_1$ and $r_2$ of equations 2-1 . . . 2-n, when a focal length of 1000 mm is substituted for $f_2$ and 1 mm is substituted for $\lambda$. Further, the actual physical aperture of electronic lens 108 in its second switch position is 63.24 mm (i.e., double the outermost radius of 31.62 mm). This is substantially equal to the design criteria physical aperture of 66.7 mm.

TABLE 3

| | Second Switch Combination | | |
|---|---|---|---|
| 1. | Lens Assembly 100 (Design Criteria) | Focal Length Physical Aperture Relative Aperture | 200 mm 66.7 mm ⅓ |
| 2. | Physical Lens 106 | Focal Length Physical Aperture at least | 250 mm 83.3 mm |
| 3. | Electronic Lens 108 (Design Criteria) | Focal Length Physical Aperture | 1000 mm 66.7 mm |
| 4. | Effective Electrodes | Radial Width | Outer Radius | Phase Delay |
| | 204 + 206 + 208 | 22.36 mm | 22.36 mm | ¼ cycle |
| | 210 + 212 | 9.26 | 31.62 | 0 cycle |

FIG. 3b shows third given combination of settings of switches 306 . . . 314, which selects a focal length of infinity for electronic lens 108. In this third combination, single-throw switches 314 and 312 are closed, so that signals at electrodes 214 and 212 are coupled directly to summer 302. Double-throw switches 310 and 308 are in their upper switch positions, so that signals at electrodes 208 and 206 are coupled directly to summer 302. Triple-throw switch 306 is in its upper switch position, so that signals at electrode 204 are coupled directly to summer 302.

Table 4, below, shows the assumed conditions for this third switch combination. Because in this third switch combination all of electrodes 204 . . . 214 are directly coupled to summer 302, a plane wavefront of received signals is detected by electronic lens 108 (i.e., electronic lens 108, in this third combination, has a focal length $f_2$ of infinity). Therefore, in this third combination, all of electrodes 204 . . . 214 are effectively connected in parallel and operate electrically as though they were one single circular cross section electrode having a radius of 41.67 mm (equal to the outer radius of outermost electrode 214). The outer radius of 41.67 mm of electrode 214 is selected to provide electronic lens 108 with a physical aperture of 83.34 mm (i.e., double the outermost radius of 41.67 mm), that is required to provide lens assembly 100 with the desired relative aperture of one-third.

TABLE 4

Third Switch Combination

| 1. | Lens Assembly 100 (Design Criteria) | Focal Length Physical Aperture Relative Aperture | | 250 mm 83.3 mm ⅓ |
|---|---|---|---|---|
| 2. | Physical Lens 106 | Focal Length Physical Aperture | | 250 mm at least 83.3 mm |
| 3. | Electronic Lens 108 | Focal Length Physical Aperture | | Infinite 83.3 mm |
| 4. | Effective Electrodes 204 + 206 + 208 + 210 + 212 | Radial Width 41.67 mm | Outer Radius 41.67 mm | Phase Delay 0 cycle |

Figure 4:
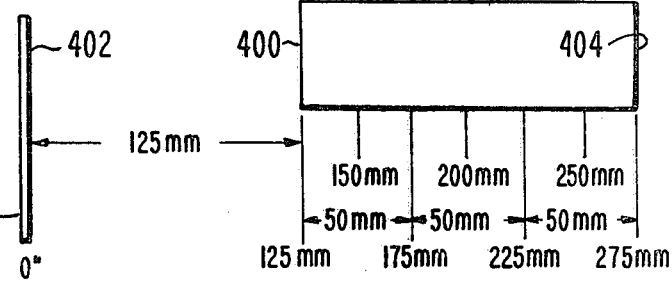
FIG. 4 is a diagram, helpful in explaining the operation of the present invention, showing an example of the respective focal lengths of a variable focal length acoustic lens employing the principles of the present invention.

Referring to FIG. 4, the front surface 400 of deep structure 102, which is to be imaged, is situated 125 mm from the effective principal plane 402 of acoustic lens assembly 100, while rear surface 404 of deep structure 102 is situated 275 mm from principal plane 402. Thus, the total depth of deep structure 102 is 150 mm.

Following the launching of each pulse of ultrasonic wave energy, time control 110 operates the switch means to maintain summer 302 decoupled from transducer 114 until a first given time at which echoes originating at front surface 400 are received by transducer 114. At this first given time, time control 110 operates the switch means to their first given switch combination so that acoustic lens assembly 100 exhibits a focal length of 150 mm. This first given switch combination is maintained until a second given time at which echoes originating 175 mm from principal plane 402 are received by transducer 114. At this second given time, time control 110 operates the switch means to their second given switch combination, so that acoustic lens assembly 100 exhibits a focal length of 200 mm. This second given switch combination is maintained until a third given time at which echoes originating 225 mm from principal plane 402 are received by transducer 114. At this third given time, time control 110 operates the switch means to their third switch combination, so that lens assembly 110 maintains the switch means in their third switch combination until echoes originating 11 inches from principal plane 402 are received by transducer 114.

It is necessary that all echoes received by transducer 114, that originate at points within deep structure 102, remain within the depth of focus of variable focal length acoustic lens assembly 100, in order that they may be imaged in focus on B-scan display 120. It can be seen from FIG. 4 that this condition is met so long as the depth of field of acoustic lens assembly 100 for each preselected focal length is at least 25 mm. As is known, the depth of field of an acoustic lens is equal to the product of four times the wavelength of the ultrasonic wave energy divided by the square of the relative aperture. The assumed value of wavelength is 1 mm and the assumed relative aperture is one-third. These assumed values provide a depth of field in excess of 25 mm.

In the preferred embodiment of coupling means 112, shown in FIG. 3, the electronic lens 108 exhibits a focal length of infinity during the launching of each pulse of ultrasonic wave energy. This is desirable because it simplifies the structure of isolation circuit 300. However, it should be understood, that isolation circuit 300, alternatively, may include appropriate phase delay circuits to provide electronic lens 108 with a desired focal length other than infinity (in accordance with equations 2-1 . . . 2-n).

What is claimed is:

1. An acoustic variable focal length lens assembly exhibiting a certain fixed relative aperture, said assembly comprising first and second serially spaced acoustic lenses for focusing acoustic wave energy of a predetermined wavelength, wherein said first acoustic lens has a given physical aperture and a single relatively short predetermined focal length, and wherein said second acoustic lens includes means for electronically controlling the focal length of said second acoustic lens to have any selected one of a predetermined plural number of different preselected discrete focal lengths, each of said discrete focal lengths being substantially larger than said predetermined focal length, and simultaneously controlling the size of the physical aperture of said second lens, in correspondence with the selection of each different discrete focal length, to have those respective values of size, no greater than said given physical aperture, which result in said assembly exhibiting substantially the same certain relative aperture for all of said different discrete focal lengths, whereby both the depth of field and the imaging resolution of said lens assembly at said predetermined wavelength and at all of said different discrete focal lengths have substantially fixed values that depend solely on said certain relative aperture of said lens assembly.

2. The acoustic lens assembly defined in claim 1, wherein the respective values of said discrete focal lengths are preselected such that the location of said respective depths of field of said lens assembly at said different discrete focal lengths are in abutting or overlapping relationship.

3. The acoustic lens assembly defined in claim 1, wherein said first acoustic lens is comprised of material exhibiting an index of refraction to said acoustic wave energy propagated therethrough which is different from that of its surroundings, and wherein said second acoustic lens comprises an electro-acoustic transducer including a piezoelectric slab having at a face thereof a plurality of separate spatially distributed electrodes and said second acoustic lens further comprises signal coupling means, including phase delay means and switch means, selectively connecting any of certain combinations of said electrodes to a common terminal to thereby select a corresponding one of said predetermined plural number of different preselected discrete focal lengths.

4. The acoustic lens assembly defined in claim 3, wherein said first lens has a given physical aperture, wherein said plurality of electrodes comprise a central electrode having a circular cross section of a preselected diameter surrounded by a certain plural number of contiguous annular electrodes with the outer diameter of the outermost one of said electrodes defining a maximum physical aperture for said second lens which is no greater than said given physical aperture, each of said annular electrodes having a preselected inner diameter and a preselected outer diameter, wherein said coupling means, when selecting the largest of said preselected discrete focal lengths, couples all of said electrodes to said common terminal and thereby exhibits a certain numerical aperture for said lens assembly, wherein said coupling means, when selecting any non-longest preselected discrete focal length, couples some given combination of electrodes, consisting of a certain non-outermost annular electrode and those electrodes surrounded by that certain non-outermost annular electrode, to said common terminal, and wherein said electrode diameters are preselected so that said combination exhibits substantially said certain numerical aperture for said lens assembly.

5. The acoustic lens assembly defined in claim 4, wherein said combination of electrodes comprises an inner group of one or more contiguous electrodes and an outer group of one or more contiguous electrodes, and wherein, in response to the selection of said non-longest preselected discrete focal length, said switch means includes means for respectively connecting in parallel said electrodes of said inner group to said common terminal and connecting in parallel said electrodes of said outer group to said common terminal and said phase delay means includes means for phase delaying signals at the freqency of said acoustic wave energy which are coupled between said electrodes of said inner group and said common terminal substantially an integral number of quarter wavelengths with respect to signals at the frequency of said acoustic wave energy which are coupled between said electrodes of said outer group and said common terminal.

6. The acoustic lens assembly defined in claim 5, wherein the electrodes of said inner and said outer groups are in contiguous serial relationship, and wherein said phase delay means includes means for phase delaying said signals coupled between electrodes of said inner group and said common terminal substantially one-quarter wavelength with respect to said signals coupled between said electrodes of said outer group and said common terminal.

7. The acoustic lens assembly defined in claim 5, wherein said given combination of electrodes further comprises an intermediate group of one or more contiguous electrodes situated between the electrodes of said inner group and the electrodes of said outer group in contiguous serial relationship therein, and wherein, in response to the selection of said nonlongest preselected discrete focal length, said switch means includes means for connecting in parallel said electrodes of said intermediate group to said common terminal and said phase delay means includes means for respectively phase delaying signals at the frequency of said acoustic wave energy which are coupled respectively (1) between said electrodes of said intermediate groups and said common terminal and (2) between said electrodes of said inner group and said common terminal by (1) substantially one-quarter wavelength and by (2) substantially onehalf wavelength with respect to signals at the frequency of said acoustic wave energy which are coupled between said electrodes of said outer group and said common terminal.

8. In an ultrasonic pulse-echo imaging system for imaging a deep structure insonified with a pulse of ultrasonic wave energy of a predetermined wavelength, the combination including:

an acoustic variable focal length lens assembly situated in spaced relationship with said deep structure so as to receive ultrasonic echoes from said insonified deep structure during a certain time interval following the insonification of said deep structure, wherein said lens assembly has a certain fixed relative aperture and comprises first and second spaced acoustic lenses, said first lens having a given physical aperture and a single relatively short predetermined focal length, and said second lens having a variable physical aperture and being electronically controlled to have any selected one of a predetermined plural number of different discrete focal lengths, each of said discrete focal lengths being substantially larger than said predetermined focal length, the respective values of said discrete focal lengths being selected such that at said predetermined wavelength the respective depths of field of said lens assembly at the respective different discrete focal lengths include separate contiguous portions of the entire depth of said deep structure to be imaged, said variable physical aperture of said second lens being controlled, in correspondence with the selection of each different discrete focal length, to have those respective values of size, no greater than said given physical aperture, which result in said assembly exhibiting substantially the same certain relative aperture for all of said different discrete focal lengths, and time-control means responsive to the time of transmission of said pulse of ultrasonic wave energy, said time-control means being coupled to said second lens for sequentially selecting each of the different discrete focal lengths during successive portions of said certain time interval to provide an effective resultant depth of field for said lens assembly which includes the entire depth of said deep structure to be imaged.

* * * * *